United States Patent [19]

Webb et al.

[11] Patent Number: 5,151,502
[45] Date of Patent: Sep. 29, 1992

[54] METHOD FOR SOLUBILIZING MEMBRANE RECEPTOR PROTEINS

[75] Inventors: Maria L. Webb, Neshanic Station; Hossain Monshizadegan, Lawrenceville, both of N.J.

[73] Assignee: E. R. Squibb & Sons, Inc., Princeton, N.J.

[21] Appl. No.: 693,501

[22] Filed: Apr. 30, 1991

[51] Int. Cl.$^5$ .............................. C07K 3/00; C07K 3/02
[52] U.S. Cl. ..................... 530/402; 435/70.1; 530/300; 530/316; 530/345; 530/350; 530/403; 530/404; 530/405; 530/406; 530/412
[58] Field of Search .............. 530/350, 395, 402, 403, 530/406, 412, 835, 300, 316, 333, 345, 404, 405; 435/70.1

[56] References Cited

PUBLICATIONS

Copponi, A. M., and Catt, K. J. (1980) J. Biol. Chem. 255, 12081–12086, "Solubilization and Characterication of Adrenal and Uterine Angiotensin II Receptors after Photoaffinity Labelling".

Forget, G. and Heisler, S. (1979) Experientia 35, 125–126 "Effect of various solubilizers on angiotensin II receptors in bovine adrenocortical plasma membranes".

Rogulja, I., King, S., Erickson, J., Abhold, R., and Harding, J. W. (1986) J. Hypertension 4, S440–S442, "Solubilized Angiotensin Receptors from Bovine Adrenal Corte: Comparison of 125-I-ANG II and 125-I--Sar(1),11e(8)-ANG II Binding".

Capponi, A. M., Birabeau, M. A., and Vallotton, M. B. (1983) J. Receptor Research 3, 289–299 "Solubilization of Adrenal Angiotensin II Receptors With a Zwitterionic Detergent".

Marie, J., Seyer, R., Lombard, C., Desarnaud, F., Aumelas, A., Jard, S., and Bonnafous, J-C. (1990) Biochemistry 29, 8943–8950 "Affinity Chromatography Purification of Angiotensin II Receptor Using Photoactivable Biotinylated Probes".

Primary Examiner—Merrell C. Cashion, Jr.
Assistant Examiner—Andrew G. Rozycki
Attorney, Agent, or Firm—Ellen K. Park

[57] ABSTRACT

A process for solubilizing membrane receptor proteins which includes exposing an outer membrane having the desired protein to an oxidizing agent, treating the membrane with a detergent and treating with an inhibitory material lowering agent. This method maintains the activity of the membrane proteins after solubilization.

5 Claims, 5 Drawing Sheets

METHOD FOR SOLUBILIZING MEMBRANE RECEPTOR PROTEINS

BACKGROUND OF THE INVENTION

Membrane receptor proteins may be targets for therapeutic intervention and therefore physical characterization and elucidation of receptor structure are important solubilization and purification of the receptor proteins are essential steps in physical characterization. A major drawback to physical characterization and purification has been the difficulty in solubilizing the proteins in a sufficiently stable and active form.

The use of detergents to solubilize receptor proteins has been employed in either pre- or post-ligand binding. However, problems have been associated with both procedures. When the protein has been solubilized prior to ligand binding, protein stability is decreased and recovery is typically low (in the order of about 5%). Where the protein has been solubilized after ligand binding, protein stability is increased (to about 50%) however, the binding analysis of the receptor protein is not possible. Therefore a method for solubilizing desired proteins while maintaining both stability and the possibility of performing binding analyses is needed.

The AII receptor represents a potential site of intervention in the development of new drugs for therapy of hypertension. However, purification of the AII receptor has proven technically difficult. The inability to solubilize sufficient amounts of AII receptor protein from cell membranes in a form capable of binding radioligand has hindered progress in this area. A primary problem in this regard has been the rapid loss of binding after solubilization of the AII receptor with ionic and nonionic detergents. More recently, the zwitterionic detergent 3-[(3-cholamidopropyl)-dimethylammonio]1-propanesulfonate (CHAPS) has been used to solubilize AII receptors from the bovine adrenal and rat adrenal glomerulosa. However, specific [$^{125}$I]-AII binding to CHAPS solubilized protein was labile with a 50% loss occurring in 10 days. In order to overcome these limitations, membranes have been solubilized from target tissues after photoaffinity labeling of AII receptor sites. A drawback to this approach is that prelabeling of membranes with photoaffinity ligands typically results in high nonspecific binding and precludes the evaluation of pharmacological characteristics of the soluble receptor. Despite this recent progress in the development of photoaffinity ligands and advances in small scale purification of the AII receptor, this protein has not been solubilized in a form which allows full pharmacological evaluation or which leads to purification. Therefore, there is a need for a method which will solubilize membrane proteins, including AII receptors in a form suitable for pharmacological characterization and biochemical purification.

BRIEF DESCRIPTION OF THE INVENTION

Figure 1:
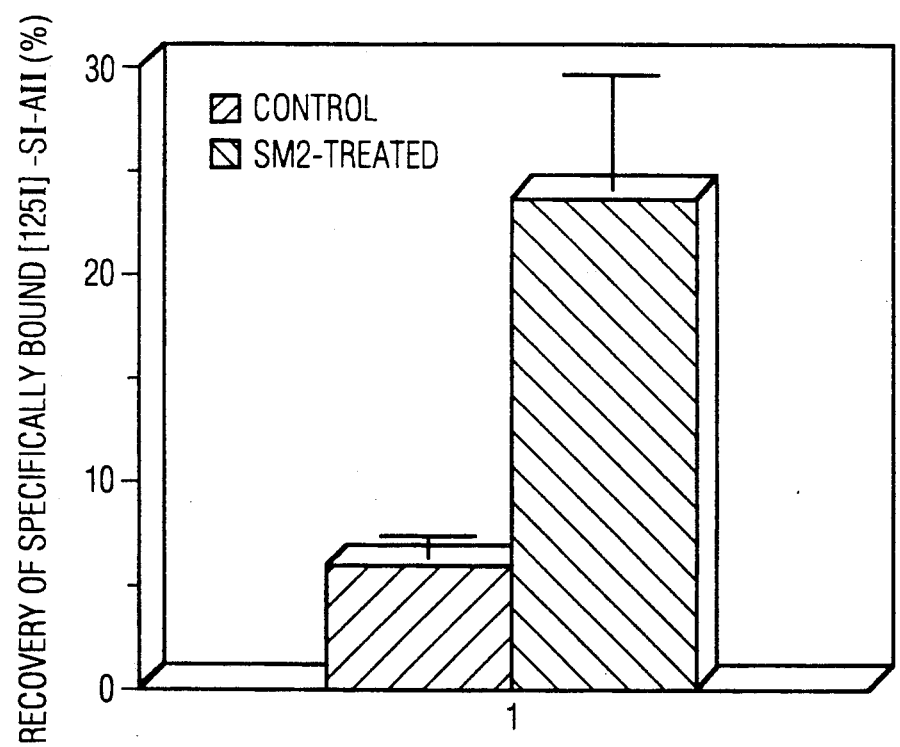
FIG. 1 shows the effect of SM2 TM bead treatment on [$^{125}$I]-SI-AII binding to solubilized bovine adrenal microsomal membranes (BAMM). Results are the mean and standard error of three experiments.

In accordance with the present invention, a process is provided for solubilizing membrane receptor proteins which are targets of reducing agents. The process comprises obtaining an outer membrane having the desired protein, exposing said membrane to an oxidizing agent, treating the membrane with a detergent to extract and solubilize the protein, and treating the membrane derived protein with a inhibitory material lowering agent.

DETAILED DESCRIPTION OF THE INVENTION

The following definitions apply throughout this specification, unless otherwise limited in specific instances.

Oxidizing agent as used herein means a compound which gains electrons. Preferred oxidizing agents include dithionitrobenzoic acid (DTNB).

Detergents as used herein means a compound to extract lipids, proteins and carbohydrates and includes anionic, nonionic and zwitterionic agents. Preferred detergents are zwitterionic detergents and include the commercially available detergents, 3-[(3-cholamidopropyl)dimethylammonio]-1-propanesulfonate (CHAPS) and Zwittergent 3-14.

Inhibitory material lowering agent as used herein means an agent which will lower the amount of undesired materials such as excess detergent and/or any material which may interfere with the binding reaction of the receptor protein. Exemplary inhibitory material lowering agents include anionic detergent removing resins and chromatography matrices. Preferred inhibitory material lowering agents are the commercially available SM2 beads, which are polymeric macroporous beads having a natural charge; Extracti-Gel D, which is a gel having a base support with an exclusion limit of 10,000 MW; and Sephadex G50, which is a hydrophillic bead formed gel, having a cross-linked Dextran structure, the beads are 20–300 micrometers in size. Inhibitory material lowering agents also include separation methods which will separate molecules less than about 10,000 daltons from molecules greater than 10,000 daltons. An example of a separation method is dialysis bags.

The method of the invention may be utilized to solubilize proteins which are targets of reducing agents while maintaining their ligand binding ability. Membrane proteins which are targets of reducing agents are those whose ligand binding abilities are inactivated by reducing agents. Examples of membrane proteins which are potential targets of reducing agents are AII receptor, thromboxane receptor and neuropeptide Y receptor. Examples of reducing agents are dithiotheitol and β-mercaptoethanol.

Microsomal membrane preparation is conducted according to methods known to those skilled in the art and disclosed in Chiu et. al. "Non-peptide Angiotensin II Receptor Antagonists. II. Pharmacology of S-8308" European J. Pharmacology 157, 13–21, 1988.

Membranes in a neutral pH buffer are incubated with oxidizing agent at a protein: oxidizing agent ratio of 1:0.1–0.5, preferably about 0.05 to 0.5 mM DTNB. Examples of neutral pH buffers are Tris buffer containing magnesium salts and 4-(2-hydroxyethyl)-1-piperazineethane-sulfonic acid buffer containing magnesium salts. It may be preferable to also include protease inhibitors as known in the art (Rondeau et. al., "Hydrodynamic properties of the Angiotensin II Receptor From Bobine Adrenal Zona Glonerulosa," Biochem J. 268, 443–448; 1990). In addition, polyols such as sucrose, glycerol and polyethylene glycol may be included in the buffer during solubilization.

Membranes are treated with detergent at a protein:detergent ratio of 1:1 or 1:2. A preferred detergent is CHAPS at a concentration of about 1 to 10 mM.

The detergent treated membranes are then centrifuged at about $100,000 \times g$ to $200,000 \times g$ for about 45 minutes to 75 minutes, to separate soluble from insoluble material. The soluble material is treated with a sufficient amount of inhibitory material lowering agent to lower inhibitory material concentration. Where SM2 beads are utilized, preferred amounts are between 0.8 to 1.5 g of SM2 beads per mL of soluble material.

Several detergents were compared for their ability to solubilize BAMM protein and $[^{125}I]Sar^1Ile^8$-AII ($[^{125}I]$-SI-AII) binding activity. The detergents tested solubilized $\geq 55\%$ of the membrane protein but only as much as 5% of the $[^{125}I]$-SI-AII binding activity. Additionally, a substantial loss of total $[^{125}I]$-SI-AII binding activity in the insoluble fraction occurred.

Table I shows the effect of addition of DTNB (0.1 mM) to BAMM on the % recovery of solubilized AII receptor. Preincubation of membranes with DTNB resulted in a small (~6 to 11%) but consistent increase (1.5 to 2 fold) in recovery of solubilized $[^{125}I]$-SI-AII binding activity.

TABLE 1

| Control | DTNB |
|---------|------|
| 6.1 ± 0.8 | 11.5 ± 1.5* |

Values are means ± standard errors (n = 4).
*p < 0.05

The results of treatment with SM2 beads, a macroporous adsorbent used primarily for the removal of nonionic and anionic detergents may be seen in FIG. 1. CHAPS solubilized receptor preparation, with SM2 treatment resulted in approximately a 3 to 5 fold improvement in recovery of specific $[^{125}I]$-SI-AII binding activity.

Collectively, the DTNB pretreatment of membranes prior to solubilization and the detergent reduction by SM2 treatment of solubilized adrenal membrane protein, resulted in an approximate 30% recovery of specific $[^{125}I]$-SI-AII binding activity. This amounts to a 5 to 6 fold greater recovery than that obtained by previously known methods to solubilize unbound AII receptor. In addition, the binding activity was stable for 6 months storage at $-80°$ C.

Evidence that the AII receptor was in a soluble, rather than a particulate form, was provided by the retention of binding activity in the supernatant from the high speed centrifugation at $176,000 \times g$. Retention of activity in the supernatant of $105,000 \times g$ sedimentation is the most commonly used criterion for solubility. Additional evidence of solubility was the passage of $[^{125}I]$-SI-AII binding activity from high speed supernatants through a 0.22 μm millipore filter.

Figure 2:
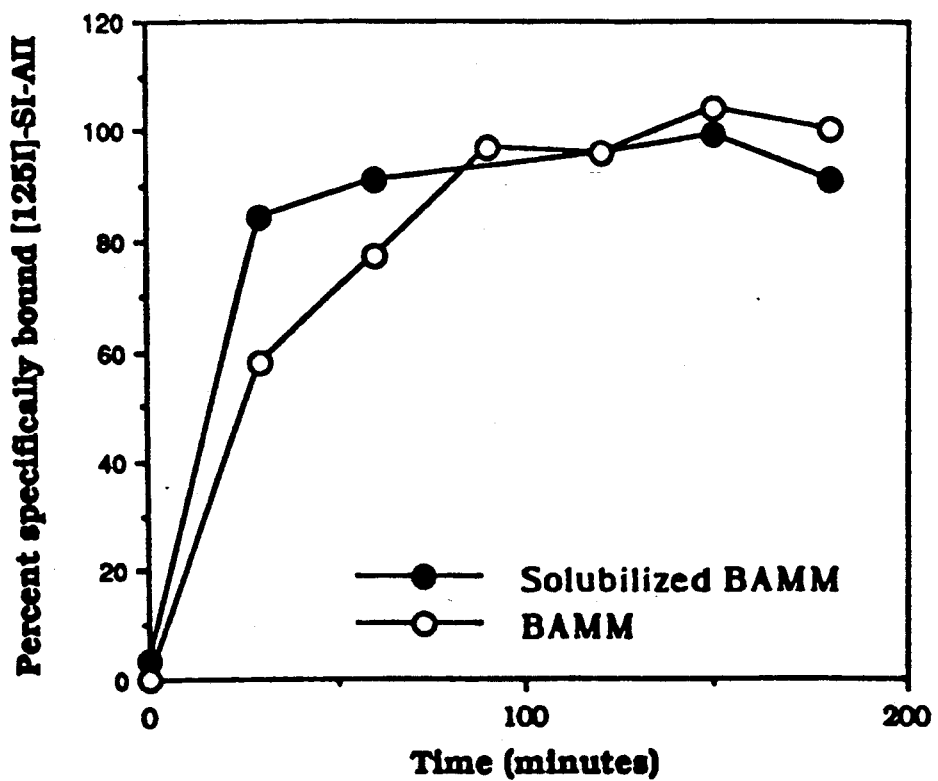
FIG. 2 shows the time course of [$^{125}$I]-SI-AII binding to bovine adrenal microsomal membranes (BAMM) and solubilized BAMM at 37° C. Results are representative of three experiments.

Pharmacological characterization of $[^{125}I]$-SI-AII binding was performed in BAMM and SM2-treated soluble AII receptor preparations. Specific $[^{125}I]$-SI-AII binding was consistently 80 to 90% of total binding in the presence of a 1000-fold molar excess of either SI-AII or AII. Binding of $[^{125}I]$-SI-AII to membrane and soluble receptor preparations reached equilibrium by 1.5 hours at $37°$ C. (FIG. 2). The specificity of $[^{125}I]$-SI-AII binding and the time to equilibrium in SM2-treated receptors is consistent with that seen in the BAMM preparation with this radioligand.

Figure 3:
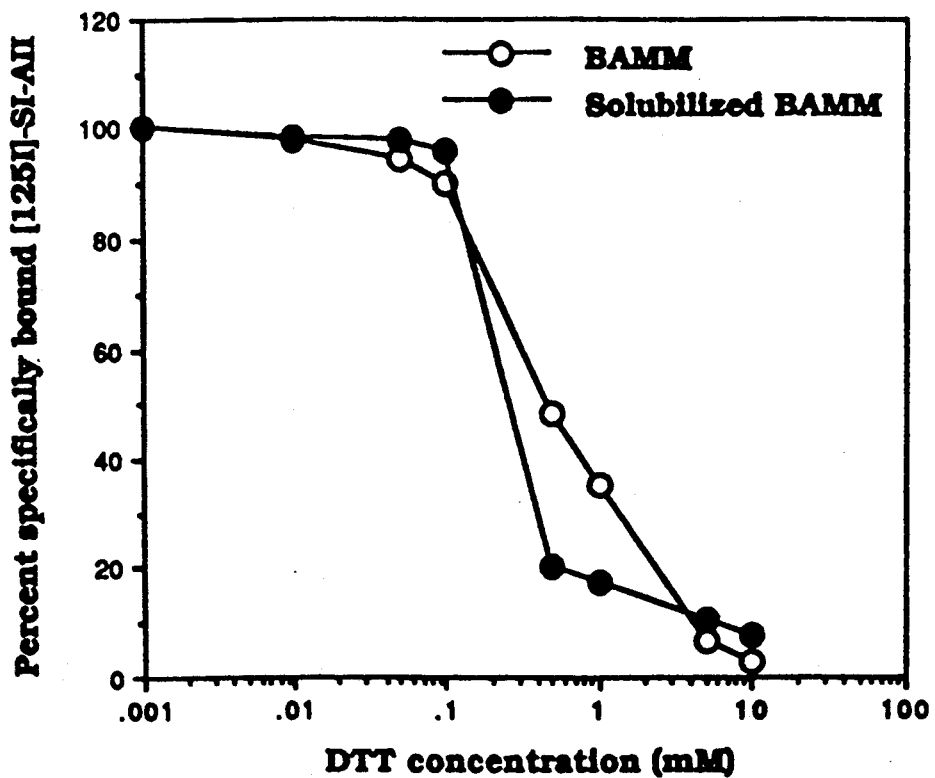
FIG. 3 shows the effect of dithiothreitol (DTT) on [$^{125}$I]-SI-AII binding to bovine adrenal microsomal membranes (BAMM) and solubilized BAMM. Results are the mean from three experiments.

The DTT sensitivity of $[^{125}I]$-SI-AII binding observed in membrane and soluble AII receptors was assessed. Specific $[^{125}I]$-SI-AII binding to membrane bound or SM2-treated soluble AII receptors was measured in the presence of increasing concentrations of DTT. As shown in FIG. 3, DTT reduced specific $[^{125}I]$-SI-AII binding to BAMM and soluble AII receptors. A 50% reduction in ligand activity occurred at a DTT concentration of 0.5 to 1 mM. At 5 mM DTT, approximately 90% inhibition of $[^{125}I]$-SI-AII binding is seen. This level of DTT sensitivity of specific $[^{125}I]$-SI-AII binding is consistent with that seen previously for AII receptors.

Figure 4A:
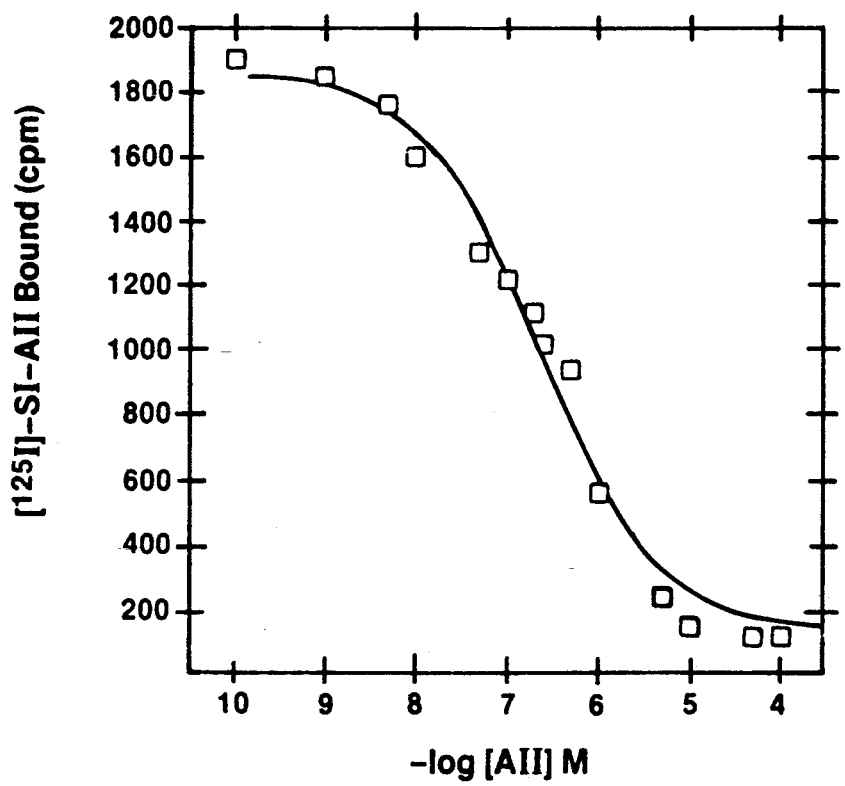
FIG. 4A shows the inhibition of [$^{125}$I]-SI-AII binding to soluble AII receptors by AII.
Figure 4B:
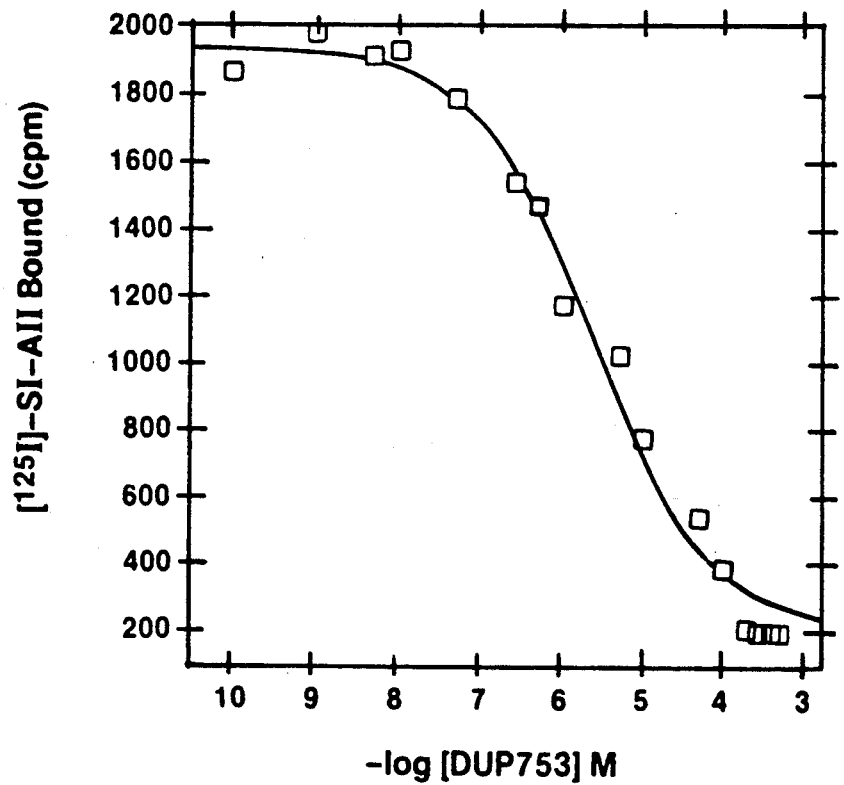
FIG. 4B shows the inhibition of [$^{125}$I]-SI-AII binding to soluble AII receptors by DuP 753.

Analysis of inhibition of $[^{125}I]$-SI-AII binding to membrane and soluble AII receptors was performed in competition experiments. Inhibition of $[^{125}I]$-SI-AII binding by AII and DuP 753 (Chiu et. al. "Identification of Angiotensin II Receptor Subtypes" Biochem. Biophys Res. Commua. 165, 196–203, 989) to SM2-treated soluble receptors was complete and indicative of a single receptor population. Table 2 and FIG. 4 show the pharmacological characteristics of membrane AII-receptor and soluble AII receptor. Inhibition of $[^{125}I]$-SI-AII binding by PD123177 (Chiu et. al. "Identification of Angiotensin II Receptor Subtypes" Biochem Biophys Res. Commua. 165, 196–203, 1989) to SM2-treated soluble receptors was negligible with an inhibition constant of greater than 100 μM. A reduction in inhibitory potency of AII and DuP 753 accompanied the solubilization of AII receptors. The $k_d$s for AII and DuP 753 increased 6 to 10 fold compared to the $k_d$s in membranes.

TABLE II

| Preparation | AII | | DuP753 | |
|---|---|---|---|---|
| | kd (nM) | Slope Factor | kd (nM) | Slope Factor |
| BAMM | 21 ± 8 | 0.81 ± 0.03 | 202 ± 22 | 0.91 ± 0.03 |
| Soluble | 126 ± 31 | 0.72 ± 0.0 | 2,540 ± 710 | 0.51 ± 0.05 |

Values are means ± SEM with n = 3 to 5.

Reductions in inhibitory potency when comparing membrane and soluble receptors have been reported for the thromboxane $A_2$/prostaglandin $H_2$, β-adrenergic and AII receptors. Such decreases in affinity of soluble receptors for their ligands have been attributed to altered conformations which the soluble receptor protein assumes when removed from the hydrophobic microenvironment of the membrane. It is well known that seven membrane spanning doamin receptors, of which the $AT_1$ receptor belongs, are dependent on the membrane for elements of their conformation and ligand binding capabilities.

Collectively, these data indicate that the $[^{125}I]$-SI-AII binding to soluble AII receptors representative of the $AT_1$ receptor subtype. The reduced specific $[^{125}I]$-SI-AII binding following DTT treatment in the SM2-treated soluble AII receptor is indicative of the $AT_1$ receptor subtype. Specific binding to $AT_1$ receptors is decreased by disulfide reducing agents whereas the binding to the $AT_2$ receptor subtype was unchanged. Although greater than that seen in the bovine adrenal membrane, the $k_d$ of DuP 753 and SM2 treated receptor is in line with the $AT_1$ receptor pharmacology in this species. It should be noted that the $k_d$ of DuP 753 receptor for bovine adrenal membrane receptors is greater than that for the rat adrenal cortex. Furthermore, binding of [$^{125}$I]-SI-AII to soluble SM2-treated AII receptors was inhibited by PD123177 at concentrations greater than 100 μM.

These data indicate that 30% of the angiotensin II receptor in bovine adrenal membranes can be recovered for biochemical or pharmacological analysis after CHAPS-solubilization. This receptor displays characteristics consistent with the $AT_1$ receptor. The $AT_2$ receptor has not been solubilized for more stringent biochemical and pharmacological examination.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

A. Microsomal Membrane Preparation

All the procedures were performed at 4° C. unless otherwise indicated. Bovine adrenals were cleaned of connective tissue and fat and were minced in 10 volumes of homogenization buffer (10 mM Tris, pH 7.4 at 4° C. containing 0.25M sucrose and 1 mM ethylenediaminetetraacetic acid). The minced tissue was homogenized using a Brinkmann polytron homogenizer (five ten second bursts at setting #8). The homogenate was centrifuged at 3,000×g (5,000 rpm) in a Sorvall SS34 rotor) for 10 minutes and the supernatant filtered through 3 layers of cheesecloth. The filtrate was centrifuged at 12,000×g (10,000 rpm in a Sorvall SS34 rotor) for 15 minutes. The supernatant was centrifuged at 102,000×g (38,000 rpm in a Beckman 60Ti rotor) for 60 minutes and the resulting pellet resuspended in buffer R ("resuspension buffer": 50 mM Tris buffer, pH 7.4 at 4° C. containing 5 mM magnesium chloride). Protein concentration was estimated using B.C.A. (Smith et. al. "Measurement of Protein Using Bicinchoninic Acid" Anal. Biochem. 150, 76–85, 1985) protein reagent using bovine serum albumin as standard. Aliquots (5 mg/ml) of the bovine adrenal microsomal membranes (BAMM) were stored at 80° C. until use.

B. Solubilization of BAMM AII Receptors

All procedures were performed at 4° C. unless otherwise noted. Solubilization of specific binding activity was carried out by incubation of BAMM with 5 mM CHAPS. Optimum solubilization was achieved with 5 mM CHAPS in the presence of 0.1 mM DTNB and a cocktail of protease inhibitors (2 mM ethylenediaminetetraacetic acid, 1 μM aprotinin, 1 μM leupeptin, 0.02% PMSF (phenylmethyl sulfonyl fluoride), 0.1 μM pepstatin A, 2 μg/ml bestatin. Prior to solubilization, membranes were incubated with 0.1 mM DTNB for 10 minutes with constant agitation. Membranes thus treated were incubated with 5 mM CHAPS in buffer S ("solubilization buffer": 50 mM Tris,pH 7.4, containing 0.25M sucrose, 10% glycerol and the protease inhibitor cocktail), for 1 hour with constant rotation. The solubilized membranes were centrifuged at 176,000×g (50,000 rpm in a Beckman 80Ti rotor) for 1 hour. The soluble BAMM preparation was stored at 80° C. Prior to assay, soluble BAMM protein was filtered through a 0.22 μm filter and treated with SM2 beads. SM2 treatment proceeded with the addition of 1.1 g (w/v) of the beads and incubation for 1 to 2 hours with constant rotation. The beads were,, removed under air pressure. Residual beads were removed from solution by microcentrifugation at 11,000×g (14,000 rpm.) for 15 minutes.

C. Radioligand Binding Assay

Assays were conducted in 1.2 ml tubes in a total assay volume of 200 μl. The incubation mixture contained 0.1 to 0.2 nM [$^{125}$I]-SI-AII and incubation buffer (50 mM Tris, pH 7.4 at 4° C., 150 mM sodium chloride, 0.1% bovine serum albumin, 0.24 TI units/ml aprotinin, 0.1 mg/ml 1,10-phenanthroline). The binding reaction was initiated by the addition of 20 to 100 μg of BAMM or soluble BAMM diluted in incubation buffer. Binding proceeded at 37° C. for 2 hours with constant agitation. Reactions were terminated and bound and free radioligand separated by rapid filtration over double-thickness glass-fiber filters which had been presoaked in 0.3% polyethyleneimine in 50 mM Tris (pH 7.4) utilizing a Tomtec TM 96-well cell harvester set at four pulse washes. Filters were counted in a RIASTAT gamma counter or washed twice, microwave-dried, and counted in a Pharmacia 1205 Beta Plate flatbed scintillation counter in the presence of a dry scintillant (Pharmacia MeltiLex Scintillator Sheets TM). Dissociation constants and slope factors were calculated according to Cheng and Prusoff (Biochem. Pharmacol. 22, 3099–3109; 1973) and Hill (J. Physiol. 40, 109–224; 1910), respectively. analysis of saturation binding data was performed using nonlinear regression least-square curve fitting to the nontransformed data or by Scathard transformation (Ann. N.Y.Acad. Sci., 51, 660672;1949).

What is claimed is:

1. A method for solubilizing membrane receptor proteins which are targets of reducing agents, said membrane receptor proteins being selected from the group consisting of angiotensin II receptor protein, thromboxane receptor protein and neuropeptide Y receptor protein, which comprises:
   a. exposing an outer membrane having said receptor protein to an oxidizing agent;
   b. treating said membrane with a detergent to extract and solubilize said protein; and
   c. treating the membrane derived proteins with an inhibitory material lowering agent, said agent being a polymeric macroporous bead having a neutral charge.

2. The method as recited in claim 1 where the oxidizing agent is dithionitrobenzoic acid.

3. The method as recited in claim 1 where the detergent is a zwitterionic detergent.

4. The method as recited in claim 3 where the detergent is 3-[3-cholamidopropyl)-eimethylammonio]1-propane sulfonate.

5. The method as recited in claim 1 where the inhibitory material lowering agent is SM2 beads.

* * * * *